United States Patent [19]

Schwartz, deceased

[11] Plant 4,711

[45] May 12, 1981

[54] ROSE PLANT

[75] Inventor: Ernest Schwartz, deceased, late of Kingsville, Md., by Hazel E. Schwartz, executrix

[73] Assignee: Nor'East Miniature Roses, Inc., Rowley, Mass.

[21] Appl. No.: 142,412

[22] Filed: Apr. 21, 1980

[51] Int. Cl.[3] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

The new pale pink colored miniature rose with yellow tones, excellent hybrid tea-like exhibition form and excellent substance.

1 Drawing Figure

1

The present invention relates to a new and distinct variety of rose plant of the miniature rose class, which was originated by my crossing as seed parent the rose known as "Charlie McCarthy" and an unnamed, unreleased and unpatented seedling of my creation as pollen parent.

Among the novel characteristics possessed by this new variety which distinguish it from its parents and all other varieties of which I am aware are its pleasant pale pink coloring with yellow tones, excellent exhibition form and substance, borne singly to a stem in a manner typical of hybrid tea plants and occasional clusters and which lighten upon aging. The many petaled flowers are borne on an upright, compact, uniform branching plant. Asexual reproduction by budding of the new variety as performed in Essex County, Mass., shows that the foregoing and other distinguishing characteristics come true to form and are established and transmitted through succeeding propagations.

The new and improved rose variety which I have developed has flowers of particularly attractive bud and flower form and large thick petals which spirally unfurl and are delightfully displayed against attractive green foliage. The flower color lightens upon aging resulting in an eye-catching plant for display with varying pale pink, yellow and near white color tones often visible at the same time.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "16C" is plate 16C of the Royal Horticultural Society Color Chart.

Parentage: Seedling.

*Seed parent.*—"Charlie McCarthy".

*Pollen parent.*—Unnamed, unreleased seedling.

Class: Miniature.

The following observations are made of specimens grown in Essex County, Mass., during the month of February.

2

1. FLOWER

Blooming habit: Fast recurrent.

A. Bud (1) *Size.*—Medium.

(2) *Form.*—High centered, urn shaped.

(3) *Color.*—When sepals first divide, underside of outer petals first seen feature buttercup yellow coloring (16C) of petals at and near point of attachment, lightening to near white toward the petal edge. However, immediately upon unfurling, outer petals reflex downward showing pinkish colored edge 56D of the top surface of outer petals.

(4) *Sepals.*—Long, tapering, longer than bud.

(5) *Peduncle.*—Length — normal. Aspect — straight. Strength — erect, firm. Color — near to 145A.

B. Bloom:

(1) *Size.*—Average size when fully expanded — about $1\frac{1}{4}$ inches.

(2) *Borne.*—Singly and occasional small sprays.

(3) *Form.*—High centered at first, retaining high center until fully mature, petals spiral in formal arrangement.

(4) *Petalage.*—Number of petals under normal conditions — about 18 to 22.

(5) *Color.*—As petals spirally unfurl from buds, color density is greater at the center of the spiral. Flowers $\frac{1}{3}$ to $\frac{1}{2}$ open have excellent hybrid tea-like exhibition form and display both pinkish tones within a near white basic coloring blending into paler yellow and deeper yellow coloring to point of petal attachment. The pinkish tones remain near to 56D and the yellow tones deepen to 16D and 16C. When flowers mature the yellow coloring becomes less pronounced and the pink tones lighten.

C. Petals:

(1) *Texture.*—Thick and firm, excellent substance.

(2) *Appearance.*—Inside — velvety: Outside — satiny.

(3) *Form.*—Broadly oval, wider than long, reflexing and quilling to star-like points.

(4) *Arrangement.*—Regularly arranged, spiral-like.

(5) *Petaloids in center.*—Few.

(6) *Persistence.*—Drop cleanly.

(7) *Fragrance.*—Slight.

(8) *Lasting quality.*—Very long lasting on the plant and as a cut flower.

2. REPRODUCTIVE ORGANS

A. Stamens, filaments and anthers:
(1) *Arrangement.*—Stamens regularly arranged around styles.
(2) *Color.*—21B.
B. Pollen: Color — 21A.
C. Styles: Medium length, numerous.
D. Stigmas: Color — 2D.
E. Hips: Globular, small, color orange red, seeds sometimes protrude.

3. PLANT

A. Form: Upright, compact.
B. Growth: Vigorous, uniform branching. Height attained — 12 to 14 inches.
C. Foliage: Compound 5 to 7 leaflet leaves.
(1) *Size.*—Medium.
(2) *Quantity.*—Abundant.
(3) *Color.*—New foliage — upper side near to 137C; under side near 138B. Old foliage — upper side near to 137B; under side near 138B.
(4) *Shape.*—Pointed, oval.
(5) *Texture.*—Upper side — glossy. Under side — matte.
(6) *Edge.*—Serrate.
(7) *Serration.*—Normal.
(8) *Leaf stem.*—Color — near to 146C. Under side — near to 144C.
(9) *Stipules.*—Medium length, not bearded.
(10) *Resistance to disease.*—Blackspot — average. Mildew — average.
D. Wood:
(1) *New wood.*—Color — near 139C. Bark — smooth.
(2) *Old wood.*—Color — brownish green. Bark — smooth.
E. Thorns:
(1) *Thorns.*—Quantity — relatively few. On laterals from stalk — few. Form — long thin, slightly downward curve. Length — medium. Color (when young) — 185C. Position — irregular.
(2) *Prickles.*—Few.
F. Winter hardiness: Needs normal protection in extreme climate.

I claim:

1. A new and distinct variety of rose plant of the miniature class, substantially as shown and described, characterized particularly by pale pink and near white blooms with yellow tones at petal point of attachment, excellent bud and flower form and excellent substance.

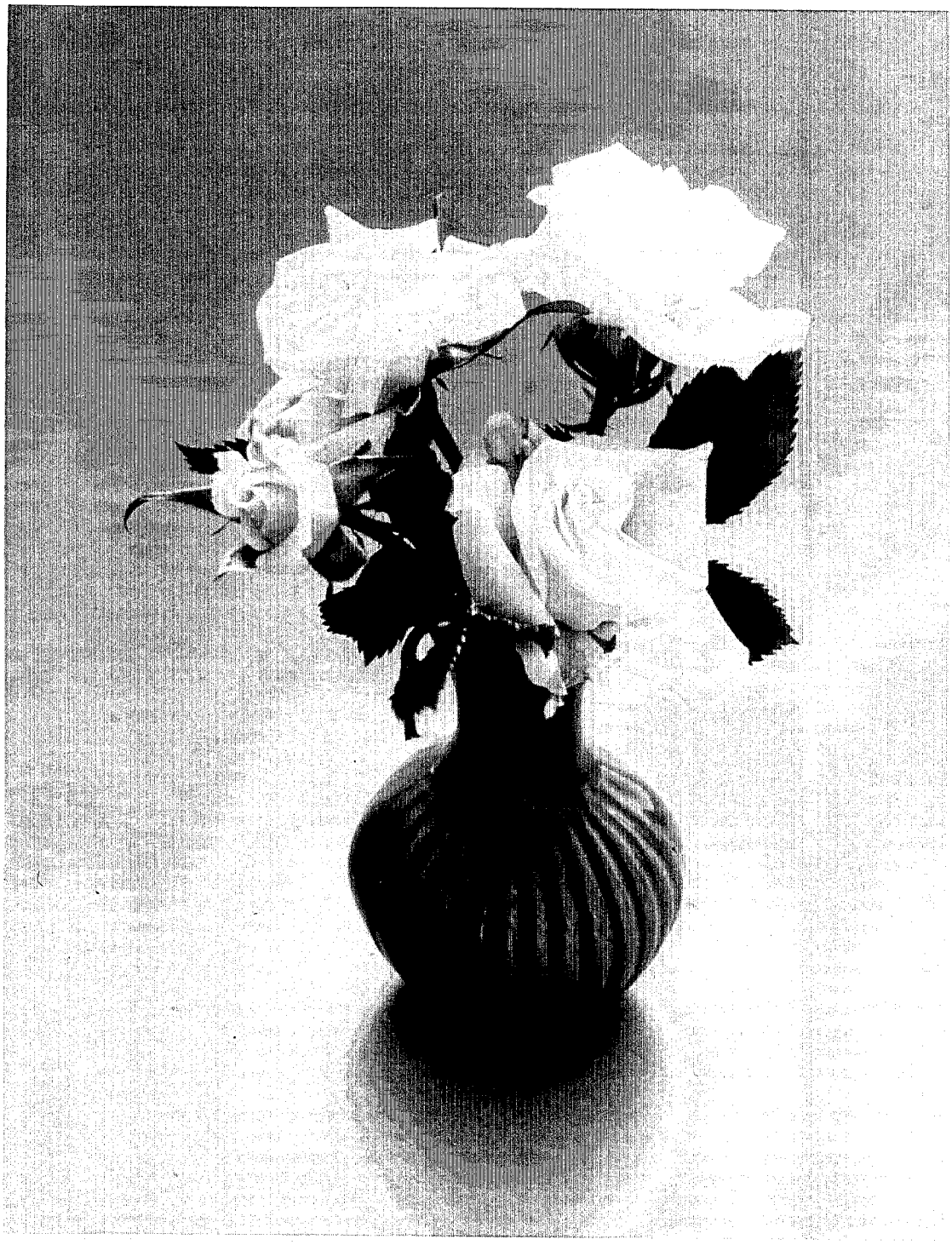

* * * * *